United States Patent
Glesener et al.

(10) Patent No.: US 6,267,866 B1
(45) Date of Patent: Jul. 31, 2001

(54) FABRICATION OF A HIGH SURFACE AREA BORON-DOPED DIAMOND COATED METAL MESH FOR ELECTROCHEMICAL APPLICATIONS

(75) Inventors: John W. Glesener, Richardson, TX (US); Paul M. Natishan, Davidsonville, MD (US); William E. O'Grady, Hyattsville, MD (US); Arthur A. Morrish, Olney, MD (US); Brian R. Stoner, Chapel Hill, NC (US); Patrick L. Hagans, Lansdale, PA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/418,355

(22) Filed: Oct. 14, 1999

(51) Int. Cl.$^7$ ........................................... C25B 3/00
(52) U.S. Cl. ................... 205/450; 205/453; 205/456; 205/463; 205/465; 205/440
(58) Field of Search .............. 204/290.01, 283, 204/284, 294; 205/440, 450, 453, 456, 463, 465

(56) References Cited

U.S. PATENT DOCUMENTS

| | | | |
|---|---|---|---|
| 4,203,821 | 5/1980 | Cramer et al. | 204/268 |
| 4,206,030 | 6/1980 | Santora | 204/242 |
| 4,444,641 | 4/1984 | Oda et al. | 204/286 |
| 5,075,094 | 12/1991 | Morrish et al. | 423/446 |
| 5,374,414 | 12/1994 | Morrish et al. | 423/446 |
| 5,399,247 | * 3/1995 | Carey et al. | 204/294 |
| 5,614,078 | 3/1997 | Lubin et al. | 205/743 |
| 5,900,127 | 5/1999 | Iida et al. | 204/290 |
| 5,911,859 | 6/1999 | Greaney et al. | 204/280 |
| 5,935,392 | 8/1999 | Lubin et al. | 204/290 |

OTHER PUBLICATIONS

Glesener, et al., Fabrication of high surface area boron--doped diamond coated tungsten mesh for electrochemical applications, Materials Letters 37, Oct. 1998, pp. 138–142.

Martin, et al., Hydrogen and Oxygen Evolution on Boron--Doped Diamond Electrodes, J. Electrochem. Soc., vol. 143, No. 6, Jun. 1996, pp. L133–L136.

Awada, et al., Electrondeposition of Metal Adlayers on Boron–Doped Diamond Thin–Film Electrodes, J. Electrochem. Soc., vol. 142, No. 3, Mar. 1995, pp. L42–L45.

Swain, The Susceptibility to Surface Corrosion in Acidic Fluoride Media: A comparison of Diamond, HOPG, and Glassy Carbon Electrodes, J. Electrochem. Soc., vol. 141, No. 12, Dec. 1994, pp. 3382–3393.

DeClements, et al., The Formation and Electrochemical Activity of Microporous Diamond Thin Film Electrodes in Concentrated KOH, J. Electrochem. Soc., vol. 144, No. 3, Mar. 1997, pp. 856–n 866.

Swain, et al., The Electrochemical Activity of Boron–Doped Polycrystalline Diamond Thin Film Electrodes, Anal. Chem., 1993, 65, pp. 345–351 No month available.

Tenne, et al., Efficient electrochemical reduction of nitrate to ammonia using conductive diamond film electrodes, J. Electroanal. Chem., 347 (1993) pp. 409–415 No month available.

Morrish, et al., Effects of surface pretreatments on nucleation and growth of diamond films on a variety of substrates, Appl. Phys. Lett. 59 (4), Jul. 22, 1991, pp. 417–419.

Morrish, et al., Diamond tubes and fibers, Diamond and Related Materials, 3 (1993), pp. 173–176 No month available.

Mort, et al., Chapter 4, Carbon Thin Films, Plasma Deposited Thin Films, CRC Press, Inc., Boca Raton, FL, pp. 89–127 No month/year available.

Angus, et al., Chemical Vapour deposition of diamond, Phil. Trans. R. Soc. Lond. A (1993) 342, pp. 195–208 No month available.

Letterinton, Applications of Diamond–like carbon thin films, Phil. Trans. R. Soc. Lond. A (1993) 342, pp. 287–296 No month available.

Robertson, Deposition of diamond–like carbon, Phil. Trans. R. Soc. Lond. A (1993) 342, pp. 277–286 No month available.

Natishan, et al., The Electrochemical Behavior of Diamond Coated Molybdenum, Materials Newsletter, vol. 8, No. 8, Aug. 1989, pp. 296–27.

Hagans et al., Electrochemical Oxidation of Phenol on CVD–Carbon Electrodes, ECS Meeting Abstracts, vol. MA99–1, 1999, p. 835 No month available.

* cited by examiner

*Primary Examiner*—Bruce F. Bell
(74) *Attorney, Agent, or Firm*—John J. Karasek; Amy L. Ressing

(57) ABSTRACT

An electrode for electrochemical uses is made of a conductive metal mesh coated with boron-doped diamond. The electrode may be used in electrochemical reactions either as a cathode or as an anode, or can be used with an alternating current.

4 Claims, No Drawings

FABRICATION OF A HIGH SURFACE AREA BORON-DOPED DIAMOND COATED METAL MESH FOR ELECTROCHEMICAL APPLICATIONS

BACKGROUND OF THE INVENTION

1. Field of the Invention

The present invention relates to an electrode for electrochemical uses and, more particularly, to an electrode made of metal mesh coated with boron-doped diamond.

2. Description of the Related Art

In recent years, there has been an increasing interest in the electrochemical properties of diamond and boron-doped diamond coated substrates, primarily due to the excellent resistance of material to chemical degradation and, as a result, its dimensional stability. The physical and electrochemical properties of boron-doped diamond have been described in the following patents and publications incorporated herein by reference: U.S. Pat. No. 5,399,247 to Carey; U.S. Pat. No. 5,900,127 to Iida et al; Swain, "The Electrochemical Activity of Boron-Doped Polyciystallinc Diamond Thin Film Electrodes" Anal. Chem 1993, 65 pp 345–351; DeClements and Swain, "The Formation and Electrochemical Activity of Microporous Diamond Thin Film Electrodes in Concentrated KOH", J. Electrochem. Soc., Vol 144, No. 3 March 1997, pp 856–866; Swain "The Susceptibility to Surface Corrosion in Acidic Fluoride Media: A Comparison of Diamond, HOPG, and Glassy Carbon Electrodes", J. Electrochem. Soc., Vol 141, No. 12, December 1994, pp 3382–3393; Tenne et al, "Efficient Electrochemical Reduction of Nitrate to Ammonia Using Conductive Diamond Film Electrodes" J. Electroanal. Chem 347 (1993) pp 409–415; Awada, "Electrodeposition of Metal Adlayers on Boron-Doped Diamond Thin-Film Electrodes" J. Electrochem Soc., Vol.142, No.3 March 1995, pp L42–L45; Martin et al, "Hydrogen and Oxygen Evolution on Boron-Doped Diamond Electrodes" J. Electrochem. Soc., Vol 143, No. 6, June 1996, pp L133–L136, and Glesener et al "Fabrication of High Surface Area Boron-Doped Diamond Coated Tungsten Mesh for Electrochemical Applications" Material Letters 37 (1998), pp 138–142.

SUMMARY OF THE INVENTION

It has now been discovered that boron-doped diamond can be used in the fabrication of a high surface area flow electrode. This is done by forming a coating of boron-doped diamond on a conductive metal mesh substrate. The mesh structure allows for enhanced mass transport of reactants when used as an electrode in an electrochemical cell. The use of conducting metal as the material that makes up the of the mesh substrate improves the conductivity and energy efficiency of the electrode. The boron-doped diamond coating provides for enhanced dimensional stability and corrosion resistance for the mesh structure.

DETAILED DESCRIPTION OF THE PREFERRED EMBODIMENT

The present invention relates to the use of a boron-doped diamond coated metal mesh as an electrode in electrochemical applications.

The conductive metal mesh of the present invention can be made of any conductive metal or alloy, including, but not limited to tungsten, titanium, tantalum, copper and alloys of these metals.

As used herein, the term "mesh" refers to a structure comprised of a grid or of interwoven conductive metal filaments. The mesh morphology provides for a porous structure having a high surface area, thereby maximizing the contact of the electrode with the solution of the electrolytic cell in which the electrode is used. Preferably, the grid segments or filaments are about 0.5 mm to about 10 mm in diameter. The spacing between grid segments or filaments can range from very fine to coarse.

The conductive metal mesh may be coated with a boron-doped diamond coating by any method known in the art for creating a doped diamond coating on a substrate. Preferably, the coating is formed by filament assisted chemical vapor deposition (FACVD), a method that is described, for example in the following patents and publications, incorporated herein by reference: U.S. Pat. No. 5,075,094 to Morrish et al.; U.S. Pat. No. 5,374,414 to Morrish et al; and Natishan and Morris "The Electrochemical Behavior of Diamond Coated Molybdenum", Materials Letters, Vol. 8 No. 8, August 1989, pp 269–272.

The electrode of the present invention has a wide potential window and therefore may be used in an electrochemical cell either as an anode to oxidize reactants or as a cathode to reduce reactants. Examples of reactants that can be treated include chlorides, bromides, organic materials and water. The electrode may be used for decomposition reactions or other reactions that cannot normally be run on metal electrodes because of the high hydrogen overvoltage on the diamond surface. One example of would be the dehalogenation of organic materials as a reduction reaction at the cathode. The electrode may also be used with an aerated solution to produce peroxide, peroxide radicals and hydroxy radicals that, in turn, act as a reactant in the decomposition of organic materials not in contact with the diamond electrodes. Oxygen may be added at the cathode side to increase the amount of peroxide that is produced. Because of the dimensional stability of the electrode, it may be used with an alternating current to function cyclically as both an anode and a cathode. An ac signal may be desirable for some applications where a prolonged dc current could produce undesirable reactions such as a polymerization reaction.

Having described the invention, the following examples are given to illustrate specific applications of the invention, including the best mode now known to perform the invention. These specific examples are not intended to limit the scope of the invention described in this application.

EXAMPLES

Example 1

Electrochemical Characteristics of a Boron-Doped Diamond Coated Tungsten Mesh Electrode Boron-doped diamond was deposited on a tungsten (W) mesh (7.5 cm×3.25 cm) using a large area, filament assisted chemical vapor deposition FACVD process (2,3, 8–10). The tungsten wire in the mesh was approximately 20 $\mu$m in diameter and the inner spacing between wires (inner edge to inner edge) of the mesh was 630 to 650 $\mu$m. The FACVD system consists of: a 35 cm diameter cylindrical vacuum chamber, a large area tantalum filament, a boron nitride coated substrate heated to approximately 900° C., and a gas flow control system capable of delivering four gases at flow rates of 10 to 500 standard cubic centimeters per minute (SCCM). Growth parameters were set and consisted of a methane/hydrogen ratio of 1.2/100, and aboron/carbon ratio of 1000. The gas flow rate was adjusted to 102 SCCM and a growth pressure of 15 torr utilized. Diborane was used as the dopant source. The only sample pretreatment employed was to coat the entire tungsten mesh assembly with hydrocarbon oil in the manner as described in Natishan and Morris "The Electrochemical Behavior of Diamond Coated Molybdenum", Materials Letters, Vol. 8 No. 8, August 1989, pp 269–272. During the growth phase, the tungsten mesh was suspended approximately 3–4 mm above the substrate and approximately 1 cm below a multi-strand tantalum filament which was operating at a temperature of 2150° C. The filament temperature was monitored by a two color optical pyrometer. Upon placing the substrate in the deposition chamber, the chamber is back filled several times with the process gas mixture in order to purge any oxygen out of the system. Once the desired growth conditions are reached the filament and the sample heaters are activated. Under these conditions and consistent with the results of the Morris and Natishan reference cited above, the oil coating appears to produce a thin carbide layer on the tungsten wire mesh which provides a superior nucleation environment. Given the morphology of the substrate, emphasis was placed on achieving a uniform coating over the mesh and so the diamond growth rate averaged on the order of 1 micron/hr.

The surface was characterized using scanning electron microscopy (SEM) and Raman spectroscopy. SEM images were obtained using the signals from the secondary electrons. Raman analysis of the samples was performed in air and at room temperature. The micrographs showed the tungsten mesh coated with boron-doped diamond and showed that the diamond coating completely covered the links of the mesh with a relatively uniform thickness of 35 to 40 $\mu$m. A Raman spectrum obtained from a portion of the mesh after electrochemical testing showed a sharp peak appearing at 1331 $cm^{-1}$. A Raman spectrum obtained from a diamond standard showed the 1331 $cm^{-1}$ identification. For electrochemical testing, a single compartment electrochemical cell was used. The solutions were made with reagent grade chemicals and triply distilled water. A saturated calomel electrode, sce, was used as the reference electrode and a platinum mesh was used for the counter electrode. Potentials are reported relative to the saturated calomel electrode. The diamond mesh was immersed in 0.1M NaCl solution such that a portion of the mesh that was 11.4 $cm^2$ (3.5 cm×3.25 cm) was exposed to the solution. Cyclic voltametry was used to determine the electrochemical activity. In cyclic voltametry, the current is measured as a function of potential as the potential is perturbed in a well defined manner. An initial potential is selected and the potential is then moved (scanned) at a fixed rate to a final potential. When the final potential is reached, the scan is reversed until the initial potential is attained. The movement from the initial potential to the final potential and back to the initial potential constitutes one cycle. In this work, the initial potential was −2.0 $V_{sce}$, the final potential was +2.5 $V_{sce}$, the sweep rate was 20 mV/sec, and 25 cycles were obtained.

A DPD colorometric test was used to confirm the presence of chlorine. The DPD (N,N-diethyl-P-phenylenediamine) method is the method of choice for determining the chlorine and its aqueous derivatives.

In the cyclic voltamagrams for the 1st, 15th, and 25th cycles that were obtained in 0.1M NaCl, the trace of the cyclics, for the most part, remains fairly constant. On the forward scan, chlorine production can be observed beginning at about 1.5 $V_{sce}$. The presence of chlorine in solution was confirmed using the DPD technique. On the reverse scan, the chlorine that was produced on the forward scan is reduced back to chloride beginning at approximately 0.2 $V_{sce}$.

The cyclic voltamagrams obtained in deaerated and aerated 1.0N sulfuric acid show the cathodic production of peroxide when the solution was aerated, i.e. oxygen is bubbled into the cell and that peroxide is not produced in the deaerated solution. In the cyclic obtained in the aerated solution, oxygen is reduced (a cathodic reaction) to produce peroxide beginning at a potential of 0.2 $V_{sce}$. The anodic peak at 1.07 $V_{sce}$ corresponds to the oxidation of peroxide that was produced cathodically. The production and oxidation of peroxide are not seen on the cyclic voltamagram performed in the deaerated solution, i.e. argon is used to purge the solution of oxygen.

Example 2
Electrochemical Oxidation of Phenol Using a Boron-Doped Diamond Coated Titanium Mesh Electrode This example demonstrates that boron-doped diamond conductive mesh electrodes prepared by chemical vapor deposition (cvd) are not susceptible to fouling and low efficiency and can be used to oxidize phenol to $CO_2$. Phenol was chosen as a test compound because it is one of the most difficult organic molecules to oxidize electrochemically (see, for example, M. Gattrell and D.W. Kirk, J. Electrochem. Soc., 140, 1534 (1993), incorporated herein by reference). Phenol is well known for its rapid fouling of electrode surfaces due to formation of a blocking polymer layer produced by the polymerization of the phenoxy radicals generated in the initial stages of the reaction (See, for example, Ch. Comninellis and C. Pulgarin, J. Appl. Electrochem, 21, 703 (1991), incorporated herein by reference). This fouling results in a decrease in the active surface area and an eventual tennination of the reaction.

Electrodes were prepared by coating titanium (Ti) mesh substrates (1 cm×2 cm) with approximately 10 $\mu$m of boron-doped diamond via microwave plasma enhanced chemical vapor deposition. A two step deposition process was utilized to achieve uniform nucleation and good film adhesion. The films were characterized using scanning electron microscopy (SEM) and Raman scattering spectroscopy (Reneshaw Ramanscope) to insure complete coverage of the Ti and to establish the quality of the cvd-carbon films. X-ray Photoelectron Spectroscopy (Fisons 220iXL XPS) was also used to characterize the surface composition before and after the electrochemical experiments. X-ray photoelectron spectroscopy (XPS) measurements were made using a monochromatic Al K$\alpha$ X-ray source. The base pressure was 8×10$^{-9}$ Torr or better.

The electrochemical experiments were run with a micro flow cell (manufactured by ElectroCell AB and supplied by Electrosynthesis Company, Inc.), in which a liter of 10 mM phenol in 0.1 M $H_2SO_4$ was circulated through the anode compartment of the cell at 7 ml/sec. Only 0.1 M $H_2SO_4$ was circulated through the cathode compartment at the same flow rate. The diamond film anode and stainless steel cathode were separated by a Nafion 423 membrane. The anode was constructed by spotwelding the diamond coated Ti mesh across an opening cut into a Ti plate so that the electrolyte would flow through the opening spanned by the mesh. The mesh geometric surface area in all electrochemical experiments was ~4 $cm^2$. Power was supplied to the cell with a Topward Model 3306D dc supply (maximum output: 30 V and 6 A). The total organic carbon (TOC) was monitored as a function of time and cell current. TOC was determined by converting the organic carbon in solution to $CO_2$ by high temperature combustion. After removal of the water vapor, the $CO_2$ was determined by nondispersive IR using a LI-COR (Lincoln, NE) Model LI-6252 $CO_2$ analyzer, such as is described in Jianguo Qian and Kenneth Mopper, Analytical Chemistry 68(1996) 3090–3097, incorporated herein by reference. For the measurements, a phenol standard curve was first generated using six different carbon concentrations as phenol from 1000 to 0 mgC/L in 0.1 M $H_2SO_4$ (the solution electrolyzed in the cell initially contained approximately 700 mgC/L and 1 L was used in all experiments). The data obtained from solutions collected at various electrolysis times was then compared with the standard curve to determine TOC.

A scanning electron microscope image of a representative segment of the Ti mesh electrode onto which diamond has been deposited showed that the diamond coating was not uniform in thickness but appeared to cover the mesh. A Raman spectrum obtained from the diamond-coated mesh showed a peak at 1335 $cm^{-1}$ indicative of diamond and also showed abroad amorphous carbon line centered at 1530 $cm^{-1}$. A Raman spectrum obtained from a diamond standard had a single sharp peak at 1335 $cm^{-1}$. Less frequently observed spectra showed lower $sp^3/sp^2$ carbon ratios.

XPS was also used to characterize the as-received samples. All specta were dominated by a C 1s peak centered at 284.1 eV binding energy. A small tail to the high binding energy side of this peak was also observed which was likely due to the presence of C—O containing surface contamination. This was commensurate with the very small O 1s signal centered at 532.5 ev that was always observed. Very small amounts of S, Si and Cl contamination were also observed on some areas. There is a difficulty in using the C 1s binding energy as a fingerprint for the presence of diamond due to the similarity in C 1s binding energy for diamond, graphite and diamond like carbon (see, for example, M. N. Petukhov and A. P. Dementjev, J. Chemical Vapor Deposition, 5, 230(1997), incorporated herein by reference). This is not the case for the valence band spectrum. A valence band spectrum recorded from the as-prepared surface was an excellent match for the valence band spectrum recorded from atomically clean diamond (see, for example, H-chu. Tsai and D. B. Bogy, J. Vac. Sci. Technol. A, 5, 3287(1987), incorporated herein by reference). Thre peaks were clearly observed. The peak between 15 and 21 eV is due to emission from carbon spike bands, that from 5–10 eV from p-like bands and that from 10–15 eV from bands with mixed s and p character. The small emission centered around 23 eV is likely from O 2s orbitals. This surface is not atomically clean and there quite likely are other forms of carbon present but clearly much of the carbon is in the form of diamond, in very good agreement with the Raman results.

The goal of this example was to establish that phenol in a concentrated solution could be lowered significantly by electrochemical oxidation to $CO_2$. To establish this, the total organic carbon concentration (TOC) of the solution was monitored during the reaction. The TOC was determined for two experiments utilizing the same boron-doped diamond electrode. A plot of the TOC of the solution as a function of electrolysis time for one of the experiments showed degradation of phenol from approximately 700 to 100 mg C/L. This is equivalent to a decrease of phenol concentration from 10 mM to 1.4 mM. In these results, the TOC is decreased, demonstrating that the phenol was being oxidized to $CO_2$. The oxidation rate was independent of the current. With cell currents between 0.14 and 1.8A, the average change in concentration between the two runs was 0.2 mg C/min of electrolysis time. The anolyte temperatures were recorded at the respective cell currents of 0.38 A—28 ° C.; 0.86 A—30° C.; and 1.80 A—39° C. The higher currents caused heating of the solution but the oxidation rates were essentially unchanged.

Since the oxidation rates were essentially the same for the current range examined in this work, working at currents lower than 0.14 A appears to be desirable. Results reported by Foti et. al., Electrochem. and Solid State Letter, 2, 228 (1999), incorporated herein by reference, suggest that high $O_2$ overpotentials are necessary for complete combustion of acetic acid to occur on boron-doped diamond electrodes. Even though cyclic voltammetry shows that phenol can be oxidized at potentials well below $O_2$ evolution, complete oxidation to $CO_2$ may require higher potentials. Examination of the electrode by XPS after testing showed that a considerable quantity of oxygen was now present. Also, in addition to the peak for diamond, at least 3 different carbon species with higher binding energy values than diamond were found in the C 1s spectra. This was indicative of the presence of both aliphatic C—C and C—O linkages. In addition, depending on where the X-ray beam was focused, considerable differential charging, as indicated by large peak shifts and distortions, was observed to occur suggesting that the layer was not totally conductive. Thus, at the lower currents the potentials necessary for complete oxidation to $CO_2$ might not be achieved.

In these experiments, phenol was oxidized on boron-doped diamond coated titanium mesh electrodes for concentrations of phenol which are in the category of non-wastewater hazardous waste. The total carbon in solution was reduced from ~1% TOC to <0.1% TOC with no observable decrease in decomposition rate. This means that the reacted phenol was converted completely to $CO_2$. It should be noted that the carbon left in solution was likely not all in the form of unoxidized phenol. As noted by voltammagrams, other oxidation products besides $CO_2$ are possible. The incomplete oxidation of phenol on other electrode surfaces has produced biphenol, aliphatic alcohol, organic acid and quinone decomposition products (see, for example, M. Gattrell and D. W. Kirk, Can. J. Chem. Engr., 68, 997(1990), incorporated herein by reference.).

Obviously, many modifications and variations of the present invention are possible in light of the above teachings. It is therefore to be understood that, within the scope of the appended claims, the invention may be practiced otherwise than as specifically described.

What is claimed is:

1. A method of electrochemically reducing an organic solute in a liquid solution, the method comprising the steps of providing an electrochemical cell including a liquid solution containing an organic solute and an electrode comprising a conductive metal mesh substrate coated with boron-doped diamond, charging the electrode as a cathode, exposing the liquid solution to the electrode, and aerating the liquid solution, thereby creating peroxide, peroxide radicals and/or hydroxy radicals, whereby the organic solute becomes exposed to the peroxide, peroxide radicals and/or hydroxy radicals and is reduced.

2. The method of claim 1 wherein the organic solute is a halogenated organic solute.

3. A method of electrochemically decomposing an organic solute in a liquid solution, the method comprising the steps of providing an electrochemical cell having an electrode comprising a conductive metal mesh substrate coated with boron-doped diamond, charging the electrode with an alternating voltage, and exposing the solute to the electrode.

4. A method of electrochemically decomposing an organic solute in a liquid solution, the method comprising the steps of providing an electrochemical cell including a liquid solution containing an organic solute and having an electrode comprising a conductive metal mesh substrate coated with boron-doped diamond and having means to expose the electrode to the liquid solution, and charging the electrode as an anode.

* * * * *